United States Patent
Gall et al.

(10) Patent No.: US 10,782,374 B2
(45) Date of Patent: Sep. 22, 2020

(54) METHOD FOR PROVIDING A SELECTION OF AT LEAST ONE PROTOCOL PARAMETER FROM A PLURALITY OF PROTOCOL PARAMETERS AND A MAGNETIC RESONANCE DEVICE THEREFOR

(71) Applicant: Siemens Healthcare GmbH, Erlangen (DE)

(72) Inventors: Peter Gall, Uttenreuth (DE); Eva Rothgang, Schwaig bei Nuernberg (DE)

(73) Assignee: Siemens Healthcare GmbH, Erlangen (DE)

( * ) Notice: Subject to any disclaimer, the term of this patent is extended or adjusted under 35 U.S.C. 154(b) by 235 days.

(21) Appl. No.: 15/628,763

(22) Filed: Jun. 21, 2017

(65) Prior Publication Data

US 2017/0363700 A1 Dec. 21, 2017

(30) Foreign Application Priority Data

Jun. 21, 2016 (DE) .......................... 10 2016 211 072

(51) Int. Cl.
*G01R 33/54* (2006.01)
*G01R 33/28* (2006.01)
*G16H 40/63* (2018.01)

(52) U.S. Cl.
CPC ......... *G01R 33/543* (2013.01); *G01R 33/288* (2013.01); *G16H 40/63* (2018.01)

(58) Field of Classification Search
None
See application file for complete search history.

(56) References Cited

U.S. PATENT DOCUMENTS

| 7,051,286 B1* | 5/2006 | Stemmer ................ G16H 40/63 |
| | | 715/762 |
| 10,539,638 B2* | 1/2020 | Grodzki ............... G01R 33/543 |
| 2003/0036694 A1* | 2/2003 | Liu ...................... G01R 33/563 |
| | | 600/413 |

(Continued)

FOREIGN PATENT DOCUMENTS

| CN | 103919551 A | 7/2014 |
| DE | 102014209764 A1 | 11/2015 |
| DE | 102014210414 A1 | 12/2015 |

OTHER PUBLICATIONS

Examination Report for Chinese Application No. 201710473867.2 dated Apr. 1, 2020, and English language translation.

*Primary Examiner* — Jermele M Hollington
(74) *Attorney, Agent, or Firm* — Schiff Hardin LLP

(57) ABSTRACT

In a method for providing a selection of at least one protocol parameter from a plurality of protocol parameters for a user-defined protocol parameter setting of at least one magnetic resonance protocol for a magnetic resonance examination on a patient using a magnetic resonance device, a selection mode and a setting mode can be performed. In the selection mode, stored user-dependent parameter information can be provided and a selection of the at least one protocol parameter for a protocol parameter setting can be determined based on the stored user-dependent parameter information. In the setting mode, the determined selection of the at least one protocol parameter can be provided to the user via a user interface.

17 Claims, 3 Drawing Sheets

(56) References Cited

U.S. PATENT DOCUMENTS

| | | | | |
|---|---|---|---|---|
| 2009/0234218 A1* | 9/2009 | Washburn | .............. | A61B 5/055 600/410 |
| 2010/0237863 A1* | 9/2010 | Stemmer | ................ | A61B 5/055 324/309 |
| 2012/0190962 A1* | 7/2012 | Glaser-Seidnitzer | ........................ | G16H 40/63 600/407 |
| 2013/0275086 A1* | 10/2013 | Grodzki | ................ | G01R 33/44 702/182 |
| 2014/0195954 A1* | 7/2014 | Doshi | ................... | G06F 19/321 715/771 |
| 2014/0232397 A1* | 8/2014 | Grodzki | .............. | G01R 33/543 324/309 |
| 2015/0268321 A1* | 9/2015 | Zhai | .................... | G01R 33/288 324/309 |
| 2015/0369894 A1* | 12/2015 | Meyer | ................... | G05B 15/02 700/90 |
| 2017/0023655 A1* | 1/2017 | Grodzki | ............. | G01R 33/3804 |
| 2017/0316562 A1* | 11/2017 | Haberland | ................ | G06T 7/97 |
| 2018/0038930 A1* | 2/2018 | Kroell | .................. | A61B 5/0555 |

* cited by examiner

METHOD FOR PROVIDING A SELECTION OF AT LEAST ONE PROTOCOL PARAMETER FROM A PLURALITY OF PROTOCOL PARAMETERS AND A MAGNETIC RESONANCE DEVICE THEREFOR

CROSS REFERENCE TO RELATED APPLICATIONS

This patent application claims priority to German Patent Application No. 102016211072.1, filed Jun. 21, 2016, which is incorporated herein by reference in its entirety.

BACKGROUND

The present disclosure relates to a method for providing a selection of at least one protocol parameter from a plurality of protocol parameters for a user-defined protocol parameter setting by a user for a magnetic resonance examination.

In order to generate magnetic resonance images of a patient, it is necessary in the first instance for magnetic resonance protocols to be selected by medical operating staff. Said magnetic resonance protocols encompass a large number of protocol parameters, of which individual or indeed multiple protocol parameters must be set and/or adjusted by the medical operating staff. Because of the multiplicity of settable and/or adjustable protocol parameters it is often difficult for the medical operating staff, in particular for a member of the medical operating staff unversed in the setting and/or adjustment of protocol parameters, to make a correct parameter selection. Furthermore, the large number of settable and/or adjustable protocol parameters prevents a presentation of the settable and/or adjustable protocol parameters to the medical operating staff in the form of a simple and clearly organized overview.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
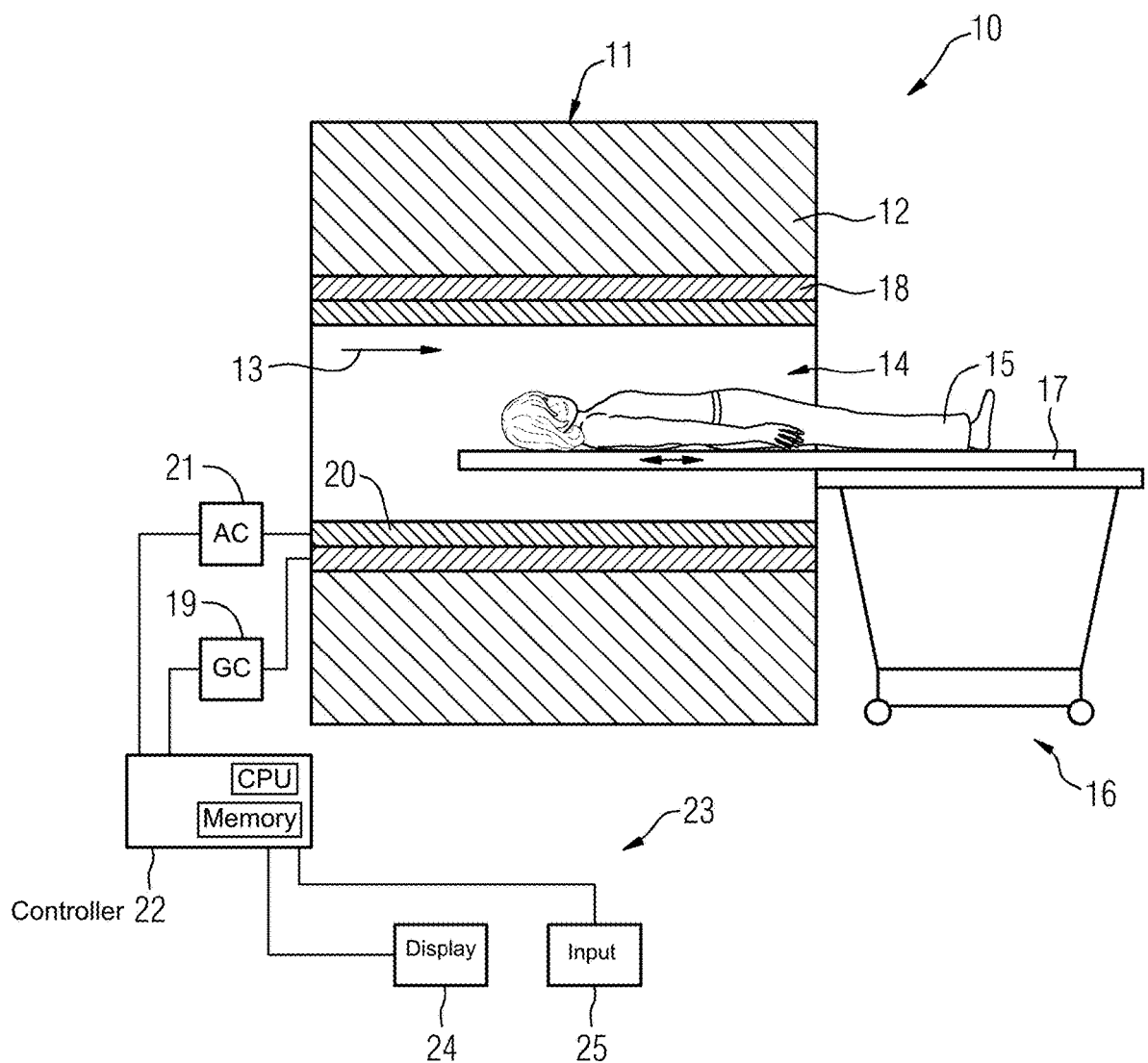
Figure 2:
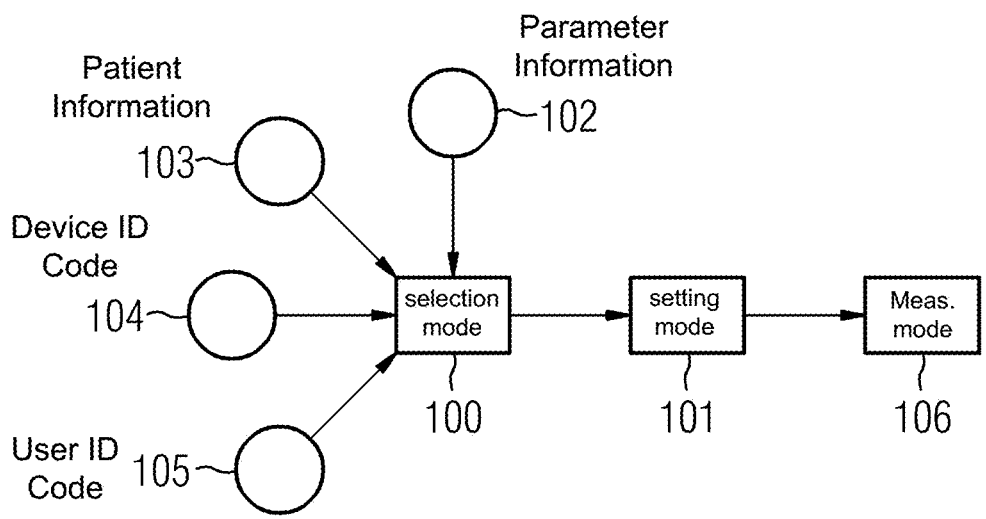
Figure 3:
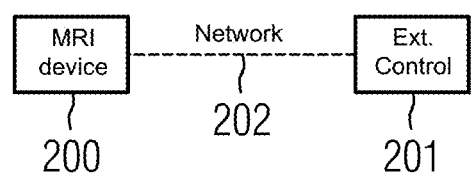

FIG. 1 is a schematic of a magnetic resonance device according to an exemplary embodiment of the present disclosure, FIG. 2 is a method for providing a selection of at least one protocol parameter from a plurality of protocol parameters for a user-defined protocol parameter setting for at least one magnetic resonance protocol for a magnetic resonance examination according to an exemplary embodiment of the present disclosure, and FIG. 3 is a schematic view of a system having a magnetic resonance device and an external controller according to an exemplary embodiment of the present disclosure.

Figure 4:
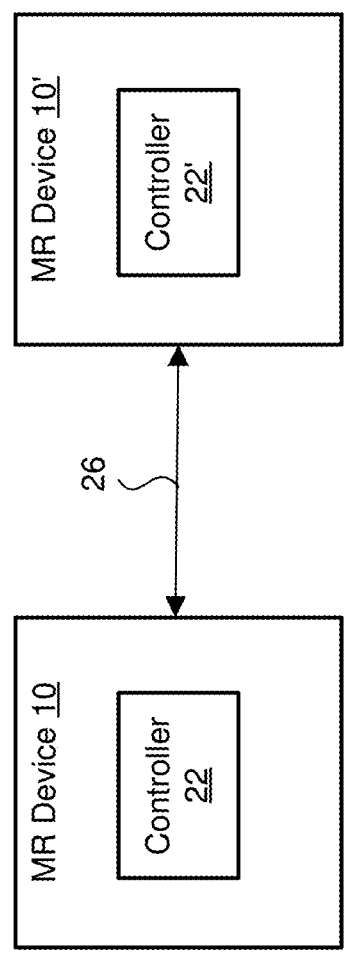

FIG. 4 is a schematic view of a system having a magnetic resonance device communicatively coupled to another magnetic resonance device according to an exemplary embodiment of the present disclosure.

The exemplary embodiments of the present disclosure will be described with reference to the accompanying drawings.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

The object underlying the present disclosure enables a simple adjustment and/or setting of protocol parameters with a clearly organized presentation of the settable and/or adjustable protocol parameters for a user.

The disclosure relates to a method for providing a selection of at least one protocol parameter from a plurality of protocol parameters for a user-defined protocol parameter setting for at least one magnetic resonance protocol for a magnetic resonance examination on a patient by a magnetic resonance device, comprising:

a selection mode, in which stored, user-dependent parameter information is provided and a selection of the at least one protocol parameter for a protocol parameter setting is determined on the basis of the stored, user-dependent parameter information, and a setting mode, in which the selection of the at least one protocol parameter is provided to the user via a user interface.

In an exemplary embodiment, what is to be understood in this context by a protocol parameter is in particular a parameter which is protocol-specific and which can be adjusted and/or set by a user, such as an echo time, for example, and/or a slice thickness and/or a slice orientation, etc. For example, a user is able to influence an image quality level by judicious selection and/or adjustment of the protocol parameters.

In an exemplary embodiment, the stored, user-dependent parameter information is stored in a memory of the magnetic resonance device. Alternatively, the stored, user-dependent parameter information may also be stored in an external memory, in which case the stored, user-dependent parameter information is provided using a data transfer. The stored, user-dependent parameter information may for example include information relating to adjustments and/or settings of individual protocol parameters. Furthermore, the stored, user-dependent parameter information may be determined on the basis of protocol parameter settings for at least one magnetic resonance protocol which comprises settings and/or adjustments of protocol parameters for prior magnetic resonance examinations. In particular, user-specific protocol adjustments and/or protocol settings may be taken into consideration in this case in the selection of the settable and/or adjustable protocol parameters. Moreover, the stored, user-dependent parameter information may also include information relating to a frequency of adjustments and/or settings of individual protocol parameters and/or a sequence with which the protocol parameters have been adjusted and/or set. Furthermore, the stored, user-dependent parameter information may also include patient-dependent information in addition.

In an exemplary embodiment, the selection mode is performed by a controller, for which purpose the controller comprises a processor. In addition, the controller has requisite computer programs and/or software which are/is executed by the processor in order to perform the selection mode. In this case the controller may comprise a central controller to which stored, user-dependent parameter information of a plurality of magnetic resonance devices may preferably be available. Alternatively, the controller may also be arranged within a magnetic resonance device, such that only the stored, user-dependent parameter information acquired on said magnetic resonance device can be included in the selection mode. The selection mode is particularly advantageously performed in a self-acting and/or automatic manner by the controller.

In an exemplary embodiment, the selection of at least one protocol parameter comprises a selection of protocol parameters of a magnetic resonance protocol which typically are adjusted and/or set by a user prior to an execution of the magnetic resonance protocol. In contrast, protocol parameters which are rarely or never set and/or adjusted by a user prior to an execution of the measurement protocol cannot be included in the selection of the protocol parameters.

In an exemplary embodiment, the selection mode comprises a learning mode in which a selection of settable and/or adjustable protocol parameters is provided as a function of the stored, user-dependent parameter information, which may comprise settings and/or adjustments of protocols that were applied in previous magnetic resonance examinations.

In an exemplary embodiment, the user interface comprises a human-machine interaction layer, wherein the disclosure enables a simplified, in particular customized and/or user-specific human-machine interaction layer to be used. The human-machine interaction layer can be displayed and/or presented for the user on a display of the user interface. The display may for example comprise a monitor and/or a screen and/or a touch display and/or a tablet computer, etc. Following a change to and/or an adjustment of the protocol parameters, a magnetic resonance measurement is performed in which the magnetic resonance protocol is executed using the changed and/or adjusted protocol parameters.

The disclosure enables a simple adjustment and/or setting of protocol parameters for a user by virtue of the fact that only the selection of protocol parameters determined in the selection step is presented to the user from this point on. An unclear and confusing presentation of all of the settable and/or adjustable protocol parameters for a measurement protocol is avoided in this case. This enables the protocol parameters to be presented to the user in the form of a clearly organized and manageable overview. Because the selection of protocol parameters is provided, and consequently because a small number of protocol parameters are presented for a setting and adjustment of the magnetic resonance protocol, it is advantageously possible to reduce an error vulnerability in the setting and/or adjustment, due for example to incorrectly selected protocol parameters, and consequently also to enhance an image quality level in the acquired image data. Furthermore, a workflow may also be simplified for the user during a preparation of the magnetic resonance examination so that the workflow can be carried out in a time-saving manner. This additionally enables a higher patient throughput and consequently increases the efficiency of the magnetic resonance device.

Furthermore, the established selection of the at least one protocol parameter can be determined in the selection mode on the basis of actuated protocol parameter settings of prior uses of the corresponding magnetic resonance protocol. Accordingly, it is likewise possible to provide a simple adjustment and/or setting of protocol parameters for a user. This likewise enables a clearly organized and manageable presentation of protocol parameters for a user. In this case the actuated protocol parameter settings of prior uses of the corresponding magnetic resonance protocol may comprise protocol parameter settings that were actuated most recently with respect to time. Furthermore, it is also conceivable that the actuated protocol parameter settings of prior uses of the corresponding magnetic resonance protocol comprise actuated protocol parameter settings that were actuated at the commencement of an application and/or use of the corresponding magnetic resonance protocol on a magnetic resonance device, in particular in the case of first-time applications and/or uses of the corresponding magnetic resonance protocol.

A further embodiment of the disclosure provides that the established selection of the at least one protocol parameter is determined in the selection mode on the basis of a frequency of a setting and/or adjustment of the individual protocol parameters that were carried out for prior magnetic resonance examinations of similar type. In an exemplary embodiment, the frequency of a setting and/or adjustment of the individual protocol parameters that were/was carried out for prior magnetic resonance examinations of similar type can be saved in the stored, user-dependent parameter information.

In particular, this enables the most frequently changed and/or adjusted protocol parameters to be added to the selection of protocol parameters. Protocol parameters that are rarely adjusted, such as in the case of special examinations, for example, are therefore not included in the selection of protocol parameters. This allows the adjustable and/or settable protocol parameters to be presented to the user in the form of a clearly organized overview.

The disclosure further provides that a selection of the at least one protocol parameter for the user-defined parameter setting is specified by a user in the selection mode using an explicit selection action. What is to be understood in this context by an explicit selection action is in particular a selection action which is performed by a user in a targeted manner and in which the user is able to specify for at least one magnetic resonance protocol that in future, during a protocol parameter setting for the magnetic resonance protocol, the protocol parameter selected by him/her or the protocol parameters selected by him/her is/are included in the selection of the protocol parameters for the user-defined parameter setting. This enables experienced users in particular to specify a selection of settable and/or adjustable protocol parameters, with the result that a simple and time-saving adjustment and/or setting of the protocol parameters can be made possible for inexperienced users.

In a further embodiment, the disclosure provides that a sequence of the selected protocol parameters is determined in the selection mode for the purpose of selecting the at least one protocol parameter on the basis of the stored, user-dependent parameter information. In this way a sequence for a protocol parameter input and/or a protocol parameter adjustment can advantageously be provided for a user. The sequence may be specified for example on the basis of a sequence of prior settings and/or adjustments of the protocol parameters that are included in the stored, user-dependent parameter information. In particular, the selected protocol parameters are provided or presented to the user in the setting mode in accordance with the determined and/or specified sequence.

Furthermore, the sequence of the selected protocol parameters can be specified in the selection mode for the purpose of selecting the at least one protocol parameter based on a sequence specified by a user using an explicit selection action. This enables experienced users in particular to specify a sequence for the selection of settable and/or adjustable protocol parameters, with the result that a simple and time-saving adjustment and/or setting of the protocol parameters can be made possible for inexperienced users.

Particularly advantageously, the selection mode and the setting mode are performed on a magnetic resonance device. In particular, the selection mode and the setting mode are performed on a single magnetic resonance device. This enables the selection mode to be performed as a function of a device-specific and/or user-specific behavior. In an exemplary embodiment, in this case, the selection mode and the setting mode are performed by a controller of the magnetic resonance device.

In a further embodiment of the disclosure it may be provided that the selection mode is performed on a first magnetic resonance device and the setting mode is performed on a second magnetic resonance device, in which case the selection of the at least one protocol parameter is exchanged between the first magnetic resonance device and the second magnetic resonance device via a data network. This enables a simple adjustment and/or setting of protocol parameters and/or also a clearly organized and manageable presentation of protocol parameters to be achieved for users at different locations. In particular this enables experienced and/or seasoned users to pass on their knowledge about the exchange of the selection of the at least one protocol parameter to inexperienced and/or untrained users.

In an alternative embodiment of the disclosure, the selection mode can be performed by an external controller, in which case stored, user-dependent parameter information of at least one magnetic resonance device is available to the external controller. In an exemplary embodiment, the controller comprises a central controller to which stored, user-dependent parameter information of a plurality of magnetic resonance devices is available. This enables a comprehensive dataset of stored, user-dependent parameter information to be made available. Furthermore, the protocol parameter settings and/or protocol parameter adjustments most frequently actuated in the past can also be taken into consideration in the selection of the at least one protocol parameter. For example, an identical selection of the at least one protocol parameter can be made available in this case to all magnetic resonance devices when the corresponding magnetic resonance protocol is called up.

It may furthermore be provided that patient information is included in the selection of the at least one protocol parameter, thereby enabling the patient information to be taken into consideration automatically already in the selection mode. This in turn enables a time-saving and simple workflow for a user. The patient information may for example be a patient's weight and/or a patient's size and/or an examination region and/or image data from prior imaging examinations, etc. The patient information may in this case be entered manually by the user. Particularly advantageously, however, the patient information is made available to the controller automatically by a radiology information system (RIS) or a hospital information system (HIS).

In a further inventive embodiment it may be provided that the at least one protocol parameter is selected as a function of a device identification code and/or a user identification code. This enables device characteristics and/or user-dependent settings to be taken into consideration in an automated manner already within the selection mode. In particular, device-specific and/or user-specific parameter information can also be provided in this way for the selection of the at least one protocol parameter. In this case different user-specific parameter information may also be saved and/or stored for different users, for example, and therefore also different selections of the at least one protocol parameter provided.

Particularly advantageously, the selection mode is performed in a self-acting and/or automatic manner using a controller. This advantageously enables user-dependent errors to be prevented in the selection of the at least one protocol parameter and consequently an amount of effort expended on the part of the user to be reduced.

The disclosure further provides that an adjustment and/or input of the at least one selected protocol parameter are/is carried out by a user in the setting mode and the adjustment and/or input of the at least one selected protocol parameter are/is stored. This enables a dataset comprising the stored, user-dependent parameter information to be constantly extended and updated. Furthermore, the latest parameter information can be made available in the selection mode and/or the learning mode at all times, such that changes in a user behavior during an adjustment and/or input of protocol parameters in the selection mode can be taken into account.

The disclosure further relates to a magnetic resonance device having a controller that is configured for performing a method for providing a selection of at least one protocol parameter from a plurality of protocol parameters for a user-defined protocol parameter setting for at least one magnetic resonance protocol for a magnetic resonance examination.

This enables a simple means of adjustment and/or setting of protocol parameters to be provided for a user, since only the selection of protocol parameters determined in the selection step is presented to the user from this point on. An unclear and confusing presentation of all of the settable and/or adjustable protocol parameters for a measurement protocol is avoided in this case. This enables the protocol parameters to be presented to the user in the form of a clearly organized and manageable overview. Because the selection of protocol parameters is provided, and consequently because a small number of protocol parameters are presented for setting and adjustment of the magnetic resonance protocol, it is advantageously possible to reduce an error vulnerability in the setting and/or adjustment, due for example to incorrectly selected protocol parameters, and consequently also to enhance an image quality level in the acquired image data. Furthermore, a workflow may also be simplified for the user during a preparation of the magnetic resonance examination so that the workflow can be carried out in a time-saving manner. This additionally enables a higher patient throughput and consequently increases the efficiency of the magnetic resonance device.

The advantages of the inventive magnetic resonance device substantially correspond to the advantages of the inventive method for providing a selection of at least one protocol parameter from a plurality of protocol parameters, which have been explained in detail in the foregoing. Features, advantages or alternative embodiment variants mentioned in this regard can equally be applied also to the other claimed subject matters, and vice versa.

In a further embodiment the disclosure relates to a system composed of a magnetic resonance device and an external controller, wherein the system is configured for performing a method for providing a selection of at least one protocol parameter from a plurality of protocol parameters for a user-defined protocol parameter setting for at least one magnetic resonance protocol for a magnetic resonance examination.

In an exemplary embodiment, the external controller comprises a central controller to which stored, user-dependent parameter information of preferably a plurality of magnetic resonance devices is available. Furthermore, the external controller is embodied independently of and/or separately from the magnetic resonance device or the plurality of magnetic resonance devices. This enables a comprehensive dataset of stored, user-dependent parameter information to be made available. Furthermore, the protocol parameter settings and/or protocol parameter adjustments actuated most frequently in the past can also be taken into consideration in the selection of the at least one protocol parameter. For example, an identical selection of the at least one protocol parameter can be made available in this case to all magnetic resonance devices when the corresponding magnetic resonance protocol is called up.

The advantages of the inventive system substantially correspond to the advantages of the inventive method for providing a selection of at least one protocol parameter from a plurality of protocol parameters, which have been explained in detail in the foregoing. Features, advantages or alternative embodiment variants mentioned in this regard can equally be applied also to the other claimed subject matters, and vice versa.

The disclosure furthermore relates to a computer program product which comprises a program and can be loaded directly into a memory of a programmable controller of a magnetic resonance device and which has program instructions and/or code for performing a method for providing a selection of at least one protocol parameter from a plurality of protocol parameters for a user-defined protocol parameter setting for at least one magnetic resonance protocol for a magnetic resonance examination when the program is executed in the controller of the magnetic resonance device. In this case the computer program may possibly require program components, e.g. libraries and help functions, in order to realize the corresponding embodiment variants of the method. The computer program may in this case comprise software having a source code which still requires to be compiled and linked or which only needs to be interpreted, or an executable software code which simply has to be loaded into a corresponding computer in order to be executed.

The disclosure furthermore relates to a computer-readable data medium comprising a program which is provided for performing a method for providing a selection of at least one protocol parameter from a plurality of protocol parameters for a user-defined protocol parameter setting for at least one magnetic resonance protocol for a magnetic resonance examination.

FIG. 1 illustrates a magnetic resonance device 10 according to an exemplary embodiment of the present disclosure. In an exemplary embodiment, the magnetic resonance device 10 includes a magnet system 11 having a superconducting main magnet 12 configured to generate a strong and in particular constant main magnetic field 13. The magnetic resonance device 10 additionally has a patient receiving zone 14 for accommodating a patient 15. The patient receiving zone 14 in the present exemplary embodiment is embodied in a cylinder shape and is cylindrically enclosed by the magnet system 11 in a circumferential direction. In principle, however, a different embodiment of the patient receiving zone 14 is conceivable at any time. The patient 15 can be introduced into the patient receiving zone 14 using a patient support and positioning device 16 of the magnetic resonance device 10. For this purpose the patient support and positioning device 16 has a patient table 17 which is embodied so as to be movable within the patient receiving zone 14.

In an exemplary embodiment, the magnet system 11 additionally has a gradient coil 18 for generating magnetic field gradients that are used for spatial encoding during an imaging session. The gradient coil 18 is controlled by a gradient controller 19 of the magnetic resonance device 10. The magnet system 11 furthermore comprises a radiofrequency antenna 20 for exciting a polarization which becomes established in the main magnetic field 13 generated by the main magnet 12. The radiofrequency antenna 20 is controlled by a radiofrequency antenna controller 21 of the magnetic resonance device 10 and radiates radiofrequency magnetic resonance sequences into an examination chamber that is substantially formed by a patient receiving zone 14 of the magnetic resonance device 10.

In an exemplary embodiment, the magnetic resonance device 10 has a controller 22 for controlling the main magnet 12, the gradient controller 19 and the radiofrequency antenna controller 21. The controller 22 is configured to centrally control of the magnetic resonance device 19, such as performing a predetermined imaging gradient echo sequence, for example. In an exemplary embodiment, the controller 22 also includes an evaluator (not shown in further detail) configured to evaluate medical image data acquired during the magnetic resonance examination.

In an exemplary embodiment, in addition, the magnetic resonance device 10 includes a user interface 23, which is connected to the controller 22. Control information such as imaging parameters, for example, as well as reconstructed magnetic resonance images can be displayed on a display 24, for example on at least one monitor and/or a screen and/or a touch display and/or a tablet computer, of the user interface 23 for a member of the medical operating staff. In an exemplary embodiment, the user interface 23 further has an input 25 configured to accept information and/or parameters entered by the medical operating staff during a measurement procedure.

In an exemplary embodiment, the controller 22 is furthermore configured to perform a method for providing a selection of at least one protocol parameter from a plurality of protocol parameters for a user-defined protocol parameter setting for at least one magnetic resonance protocol for a magnetic resonance examination on the patient 15 using the magnetic resonance device 10. In an exemplary embodiment, for this purpose the controller 22 has computer programs and/or software which can be loaded directly into a memory (not shown in further detail) of the controller 22 and which have/has program instructions/code and/or components for performing a method for providing a selection of at least one protocol parameter from a plurality of protocol parameters for a user-defined protocol parameter setting for at least one magnetic resonance protocol for a magnetic resonance examination when the computer programs and/or software are/is executed in the controller 22. For this purpose the controller 22 has a processor (not shown in further detail) which is configured for executing the computer programs and/or software. Alternatively hereto, the computer programs and/or software may also be stored on an electronically readable data medium embodied separately from the controller 22, in which case a data access can be carried out by the controller 22 to the electronically readable data medium via a data network.

In an exemplary embodiment, the method has a selection mode 100 and a setting mode 101. The selection mode 100 is executed automatically by the controller 22. In the selection mode 100, stored, user-dependent parameter information 102 is provided by the controller 22 and subsequently a selection of at least one protocol parameter, in particular for a plurality of protocol parameters, is determined for a protocol parameter setting by the controller 22 on the basis of the stored, user-dependent parameter information 102. In an exemplary embodiment, the stored, user-dependent parameter information 102 is stored in the memory of the controller 22 and/or in a memory of the magnetic resonance device 10. In principle, however, it is also conceivable for the stored, user-dependent parameter information 102 to be stored on an external memory, in which case the controller 22 is able to access the external memory using a data network.

In an exemplary embodiment, the stored, user-dependent parameter information 102 may in this case be determined on the basis of protocol parameter settings for at least one magnetic resonance protocol which comprises settings and/or adjustments of protocol parameters for prior magnetic resonance examinations. In particular, the established selection of protocol parameters is determined in the selection mode 100 by the controller 22 on the basis of actuated protocol parameter settings of prior uses of the corresponding magnetic resonance protocol. Accordingly, in an exemplary embodiment, the selection mode 100 comprises a learning mode in which a selection of settable and/or adjustable protocol parameters is provided on the basis of the stored parameter information 102, which comprises settings and/or adjustments of protocols that were applied in previous magnetic resonance examinations.

In this case the established selection of protocol parameters can be determined in the selection mode 100 by the controller 22 on the basis of a frequency of a setting and/or adjustment of the individual protocol parameters that were/was carried out for prior magnetic resonance examinations of similar type. Furthermore, it may also be provided that only the stored, user-dependent parameter information 102, which comprises the most recently actuated parameter inputs and/or parameter changes, is taken into consideration by the controller 22 in the selection mode 100. Furthermore, it is also conceivable that the actuated protocol parameter settings of prior uses of the corresponding magnetic resonance protocol comprise parameter settings and/or parameter adjustments at the start of an application and/or use of the corresponding magnetic resonance protocol on the magnetic resonance device, in particular in the case of first-time applications and/or uses of the corresponding magnetic resonance protocol.

In an exemplary embodiment, the stored, user-dependent parameter information 102 may also comprise a selection of protocol parameters specified by a user in that the selection of the protocol parameters for the user-defined protocol parameter setting is specified in the selection mode 100 as a result of a selection action performed explicitly by a user. A selection made in this way by a user is taken into consideration subsequently by the controller 22 in the selection of the protocol parameters. An explicit selection action of said type is performed in particular by experienced users, whereby said users specify a selection of settable and/or adjustable protocol parameters in order to enable inexperienced users to carry out a simple and time-saving adjustment and/or setting of the protocol parameters.

Furthermore, in an exemplary embodiment, patient information 103 can also be taken into consideration by the controller 22 in the selection of the protocol parameters. The patient information may for example be entered manually by the user. Particularly advantageously, the patient information is made available to the controller 22 by way of a radiology information system (RIS) or a hospital information system (HIS). The patient information 103 may for example comprise a patient's weight and/or a patient's size and/or an examination region and/or image data from previous imaging examinations, etc.

The controller 22 may furthermore be embodied in such a way that the selection of the protocol parameters can be performed in the selection mode 100 additionally as a function of a device identification code 104 and/or a user identification code 105. In particular, device-specific and/or user-specific parameter information may also be provided in this way for the selection of the at least one protocol parameter. At the same time, different user-specific parameter information may for example also be saved and/or stored for different users and consequently also different selections of the at least one protocol parameter may be provided.

In an exemplary embodiment, it may furthermore be provided that a sequence of the selected protocol parameters is determined by the controller 22 in the selection mode 100 for the selection of protocol parameters on the basis of the stored, user-dependent parameter information 102 and/or on the basis of the patient information and/or on the basis of the device identification code and/or on the basis of the user identification code. The sequence can be established for example on the basis of a sequence of prior settings and/or adjustments of the protocol parameters that are included in the stored, user-dependent parameter information. In particular, the selected protocol parameters are provided or presented to the user in the setting mode 101 in accordance with the determined sequence.

Furthermore, in an exemplary embodiment, the sequence of the selected protocol parameters can be specified in the selection mode 100 for the purpose of selecting the protocol parameters based on a sequence specified by a user by an explicit selection action. A selection made in this way by a user is taken into consideration by the controller 22 subsequently in the selection of the protocol parameters and their sequence. In particular, a sequence for the selection of settable and/or adjustable protocol parameters can be specified by experienced users in order to make it possible for inexperienced users to carry out a simple and time-saving adjustment and/or setting of the protocol parameters.

In an exemplary embodiment, the selection mode 100 is followed (e.g. directly or indirectly) by the setting mode 101. In the setting mode 101, the selection of protocol parameters that was made and/or determined in the selection mode 100 is provided to the user via the user interface 23, in particular the display 24 of the user interface 23.

In an exemplary embodiment, in the setting mode 101, the selected protocol parameters are set and/or adjusted by the user, wherein the latter actuates the setting and/or adjustment of the selected protocol parameters by the user interface 23, in particular by the input 25 of the user interface 23. Furthermore, the currently set and/or adjusted protocol parameters are stored and added to the dataset of stored, user-dependent parameter information 102 in the setting mode 101.

In the method described thus far, the selection mode 100 and the setting mode 101 can be performed by a single controller 22 on a single magnetic resonance device 10.

In an exemplary embodiment, with reference to FIG. 4, the selection mode 100 is performed by a first controller 22 of a first magnetic resonance device 10 and the setting mode 101 is performed on a second magnetic resonance device 10'. The selection of protocol parameters can in this case be exchanged between the first magnetic resonance device 10 and the second magnetic resonance device 10' via a data network 26. The first magnetic resonance device 10 and the second magnetic resonance device 10' may in this case be installed in the same building, such as within a hospital, for example. Furthermore, the first magnetic resonance device 10 and the second magnetic resonance device 10' may also be arranged in different buildings and/or in different countries. This enables the selection of protocol parameters to be exchanged on a global basis.

Furthermore, in an exemplary embodiment, it may also be provided that the selection mode is implemented by an external controller 201, as is represented schematically in FIG. 3. The external controller 201 comprises a central controller 201 in which data, in particular stored, user-dependent parameter information (102), of a plurality of magnetic resonance devices 200 is saved and/or stored. Only a single magnetic resonance device 200 is shown by way of example in FIG. 3, however. In an exemplary embodiment, the central controller 201 has computer programs and/or software which can be loaded directly into a memory (not shown in further detail) of the controller 201 and which have/has program instructions/code and/or components for performing a method for providing a selection of at least one protocol parameter from a plurality of protocol parameters for a user-defined protocol parameter setting for at least one magnetic resonance protocol for a magnetic resonance examination when the computer programs and/or software are/is executed in the controller 201. For this purpose, the controller 201 has a processor (not shown in further detail) which is configured for executing the computer programs and/or software. Alternatively hereto, the computer programs and/or software may also be stored on an electronically readable data medium embodied separately from the controller 22, in which case a data access by the controller 22 to the electronically readable data medium may be effected via a data network.

In an exemplary embodiment, a comprehensive dataset of stored, user-dependent parameter information may be made available for the selection mode 100 by the central controller 201. In addition, the protocol parameter settings and/or protocol parameter adjustments actuated most frequently in the past can also be taken into consideration in the selection mode 100 for the purpose of selecting the at least one protocol parameter. For example, an identical selection of the at least one protocol parameter can be made available in this case to all magnetic resonance devices 200 when the corresponding magnetic resonance protocol is called up. In this case the selection of the at least one protocol parameter can preferably be transferred via a data network 202, such as the internet, for example.

In an exemplary embodiment, the setting mode 101 is followed (e.g. directly or indirectly) by a measurement mode 106 in which the magnetic resonance protocol is performed using the set protocol parameters.

Although the disclosure has been illustrated and described in greater detail on the basis of the preferred exemplary embodiment, the disclosure is not limited by the disclosed examples and other variations may be derived herefrom by the person skilled in the art without leaving the scope of protection of the disclosure.

CONCLUSION

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g. circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g. a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

What is claimed is:

1. A method for providing a selection of at least one protocol parameter from a plurality of protocol parameters for a user-defined protocol parameter setting of at least one magnetic resonance protocol for a magnetic resonance examination on a patient using a magnetic resonance device, comprising:

in a selection mode, providing stored user-dependent parameter information corresponding to and associated with a user of the magnetic resonance device, and determining a selection of the at least one protocol parameter for a protocol parameter setting based on the stored user-dependent parameter information, the user-dependent parameter information including one or more protocol parameters having been previously defined by the user for one or more corresponding magnetic resonance protocols; and in a setting mode, providing the determined selection of the at least one protocol parameter to the user via a user interface.

2. The method of claim 1, wherein the selection of the at least one protocol parameter is determined based on actuated protocol parameter settings of one or more prior uses of the corresponding magnetic resonance protocol.

3. The method of claim 1, wherein the selection of the at least one protocol parameter is determined based on a frequency of a setting and/or adjustment of individual protocol parameters carried out for one or more prior magnetic resonance examinations of similar type.

4. The method of claim 1, wherein the selection of the at least one protocol parameter for the user-defined protocol parameter setting is specified in the selection mode by an explicit selection action by the user.

5. The method of claim 1, wherein the selection mode further comprises: determining a sequence of the protocol parameters for the selection of the at least one protocol parameter is based on the stored user-dependent parameter information.

6. The method of claim 5, wherein the sequence of the protocol parameters for the selection of the at least one protocol parameter is specified in the selection mode by a sequence specified using an explicit selection action by the user.

7. The method of claim 1, wherein the selection mode and the setting mode are performed on the magnetic resonance device.

8. The method of claim 1, wherein the selection mode is performed on a first magnetic resonance device and the setting mode is performed on a second magnetic resonance device, the selection of the at least one protocol parameter being exchanged between the first magnetic resonance device and the second magnetic resonance device via a data network.

9. The method of claim 1, wherein the selection mode is performed by an external controller configured to access the stored user-dependent parameter information of at least one magnetic resonance device.

10. The method of claim 1, wherein the selection of the at least one protocol parameter comprises patient information.

11. The method of claim 1, wherein the selection of the at least one protocol parameter is selected as a function of a device identification code and/or a user identification code.

12. The method of claim 1, wherein the selection mode is performed automatically by a controller.

13. The method of claim 1, wherein:

the selection of the at least one protocol parameter is adjusted and/or input by the user in the setting mode; and the method further comprises storing the adjustment and/or input of the selection of at least one protocol parameter.

14. A non-transitory computer program product comprising a program loadable directly into a memory of a programmable controller, the program including program instructions, that when executed by the programmable controller, control the programmable controller to perform the method according to claim 1.

15. A non-transitory electronically readable data medium having electronically readable control information stored thereon, when the control information is executed by a controller of the magnetic resonance device, instructs the controller to perform the method according to claim 1.

16. A magnetic resonance system configured to provide a selection of at least one protocol parameter from a plurality of protocol parameters for a user-defined protocol parameter setting of at least one magnetic resonance protocol for a magnetic resonance examination on a patient, the system comprising:

a memory that stores user-dependent parameter information corresponding to and associated with a user of the magnetic resonance device, and that includes one or more protocol parameters having been previously defined by the user for one or more corresponding magnetic resonance protocols; and a controller coupled to the memory configured to:

access the stored user-dependent parameter information from the memory;

determine a selection of the at least one protocol parameter for a protocol parameter setting based on the stored user-dependent parameter information; and provide the determined selection of the at least one protocol parameter via an interface.

17. The method of claim 1, wherein the user-dependent parameter information is associated with, and dependent on, the user of the magnetic resonance device.

* * * * *